United States Patent
Reed et al.

(10) Patent No.: US 7,788,980 B2
(45) Date of Patent: Sep. 7, 2010

(54) METHOD FOR GENERATION OF THZ FREQUENCY RADIATION AND SENSING OF LARGE AMPLITUDE MATERIAL STRAIN WAVES IN PIEZOELECTRIC MATERIALS

(75) Inventors: Evan J. Reed, Pine Island, MN (US);
Michael R. Armstrong, Albuquerque, NM (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 179 days.

(21) Appl. No.: 11/999,219

(22) Filed: Nov. 3, 2007

(65) Prior Publication Data
US 2009/0173159 A1 Jul. 9, 2009

Related U.S. Application Data

(60) Provisional application No. 60/872,311, filed on Nov. 30, 2006.

(51) Int. Cl.
*G01N 29/22* (2006.01)
*G01J 5/02* (2006.01)

(52) U.S. Cl. ............... 73/649; 250/341.1; 250/330; 250/338.1; 250/358.1

(58) Field of Classification Search .......... 73/649, 73/643; 250/341.1, 330, 338.1, 358.1; 600/473
See application file for complete search history.

(56) References Cited

U.S. PATENT DOCUMENTS 6,479,822 B1 * 11/2002 Nelson et al. ......... 250/341.1

| | | | |
|---|---|---|---|
| 6,957,099 B1 * | 10/2005 | Arnone et al. | 600/473 |
| 2004/0065831 A1 * | 4/2004 | Federici et al. | 250/341.1 |
| 2005/0231796 A1 * | 10/2005 | Reed et al. | 359/321 |
| 2007/0181811 A1 * | 8/2007 | Mitrofanov | 250/341.1 |
| 2007/0267574 A1 * | 11/2007 | Krug | 250/341.1 |

FOREIGN PATENT DOCUMENTS

JP 2000049403 A * 2/2000

OTHER PUBLICATIONS

Jeffrey S. Bostak, Daniel W. Van Der Weide, Ikuro Aoki, Bertram A. Auld, and David M. Bloom, "All-Electronic Generation of Sub-Picosecond Shock Waves and Their Application to a Terahertz Spectroscopy System", Jan. 25, 1993, Ultrafast Electronics and Optoelectronics (UEO), San Francisco, CA, pp. 1-4.*

J.Y. Sohn, J.S. Yahng, D.J. Park, D.S. Kim, E. Oh, J.C. Woo, G.D. Sanders, and C.J. Stanton, "Nano seismology: acoustic shock wave generation and terahertz emission from InGaN/GaN structures", Oct. 2001, Compound Semiconductors 2001, Proceedings of the Twenty-Eighth International Symposium on Compound Semiconductors, 2002, pp. 387-393.*

* cited by examiner

*Primary Examiner*—Hezron Williams
*Assistant Examiner*—Rose M Miller
(74) *Attorney, Agent, or Firm*—John H. Lee (57) ABSTRACT

Strain waves of THz frequencies can coherently generate radiation when they propagate past an interface between materials with different piezoelectric coefficients. Such radiation is of detectable amplitude and contains sufficient information to determine the time-dependence of the strain wave with unprecedented subpicosecond, nearly atomic time and space resolution.

9 Claims, 5 Drawing Sheets

METHOD FOR GENERATION OF THZ FREQUENCY RADIATION AND SENSING OF LARGE AMPLITUDE MATERIAL STRAIN WAVES IN PIEZOELECTRIC MATERIALS

This application claims priority to U.S. Provisional Patent Application Ser. No. 60/872,311, titled: "THz Frequency Radiation Generation from Large Amplitude Strain Waves", filed Nov. 30, 2006, incorporated herein by reference.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to acoustic and shock wave diagnostics, and more specifically, it relates to acoustic and shock wave generated THz radiation and the characterization of such shock acoustic and waves based on the detection of such radiation.

2. Description of Related Art

One common way of generating several cycle pulses of THz radiation using a table-top scale setup is to make use of the nonlinear effect named optical rectification, where an intense femtosecond laser pulse with a central wavelength in the optical regime produces THz power when it travels through a bulk nonlinear electro-optic crystal. The radiation generated is normally broadband which is not always desirable and the intensity is relatively low compared with other optical nonlinear techniques. The amplitude of THz radiation that can be generated during this process is limited by optical damage processes induced by the pump signal. Spatio-temporal resolution of large amplitude strain waves has been accomplished using ultrafast interferometric techniques, but interpretation of the data is generally complicated and required some degree of empirical simulation.

SUMMARY OF THE INVENTION

It is an object of the present invention to provide a method for the generation of THz radiation using acoustic and shock waves or solitons in piezeoelectric materials.

It is another object of the present invention to provide a method for the direct spatio-temporal resolution of strain waves with subnanometer and subpicosecond resolution.

These and other objects will be apparent to those skilled in the art based on the disclosure herein.

The limitations of the present method are fundamentally different from those of the prior art and are related to the strain amplitudes that can be generated in materials and the magnitudes of piezoelectric coefficients for materials. The present method generates tunable relatively narrowband radiation which is desirable for some applications like spectroscopy.

In addition to a source of THz radiation, the invention described here also constitutes a device through which large amplitude high frequency acoustic strain waves can be converted to electromagnetic radiation and detected. This method of acoustic strain wave detection does not require the complicated and often empirical post-processing that optical reflectivity approaches require because the emission occurs only from a surface.

This invention provides a source of THz radiation that can be used for imaging and spectroscopic applications in the medical, security and manufacturing sectors. Uses for THz radiation range from fundamental studies of phonon dynamics to new methods of medical and biological imaging to security screening devices able to penetrate clothing to detect explosives or other weapons.

The invention provides a large amplitude phonon detector which has potential applications ranging from acoustical imaging of nanoscale structures in materials to phonon spectroscopy to high precision timing of acoustic and shock wave propagation through materials.

The terahertz (THz) frequency range can be loosely defined as $3\times10^{11}$ to $3\times10^{12}$ Hz, with corresponding wavelengths between 100 µm and 1 mm. Situated between infrared and microwave frequencies, and between the typical reach of photonic and electronic devices, the THz range has not been thoroughly explored because of a lack of good radiation sources and detectors. THz radiation can penetrate into many materials that would be opaque at higher infrared and optical frequencies. Further, with a wavelength less than a millimeter, terahertz radiation has an important resolution advantage over the longer wavelength microwave radiation. Consequently, THz radiation is well suited for imaging and spectroscopic applications in the medical, security and manufacturing sectors. Nevertheless, the largest weakness of this field of research is still the lack of high-power, compact and low-cost sources of THz radiation.

Figure 1:
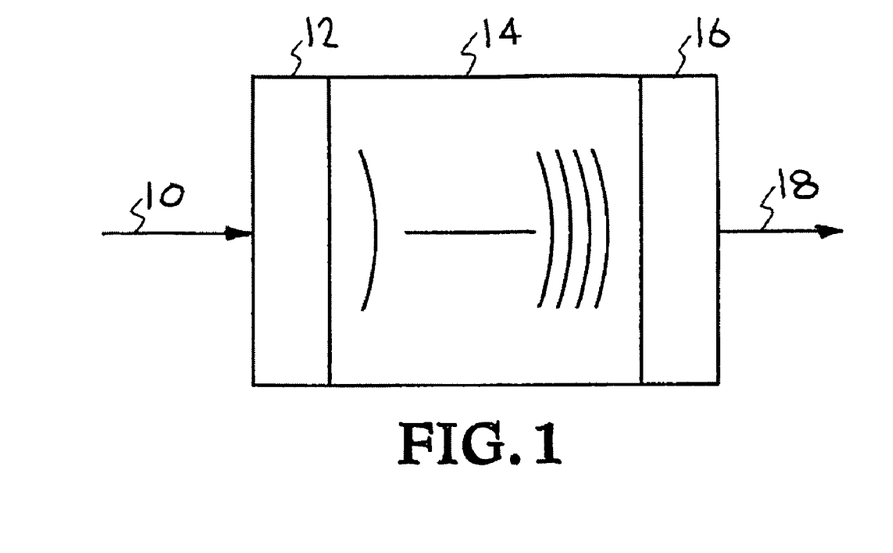
FIG. 1 is a schematic of the invention showing a shock wave generated through a laser ablation process where the shock propagates through a "hard" material (with large elastic moduli) like GaN and forms strain oscillations at the front that generate oscillating polarization currents at the interface with a piezoelectric material on the right side, generating THz frequency radiation.

The present invention, in one particular embodiment, is a new technique for the generation of THz radiation from THz frequency strain waves associated with a shock wave or soliton. FIG. 1 schematically depicts the generation of a shock wave or soliton in a material using a laser ablation process and the subsequent generation of THz radiation. In the figure, a pump beam 10 ablates material from an ablation layer 12 and drives the shock or soliton into the adjacent material 14. If the adjacent material is a "hard" material like GaN or diamond with large elastic moduli, then the strain wave will tend to form oscillations as it propagates. The oscillations fall within the THz frequency regime. When the oscillations reach piezoelectric element 16, the oscillations in strain are converted to electric polarization currents at the interface and THz electromagnetic radiation 18 is generated with temporal behavior matching that of the strain pulse.

Figure 2:
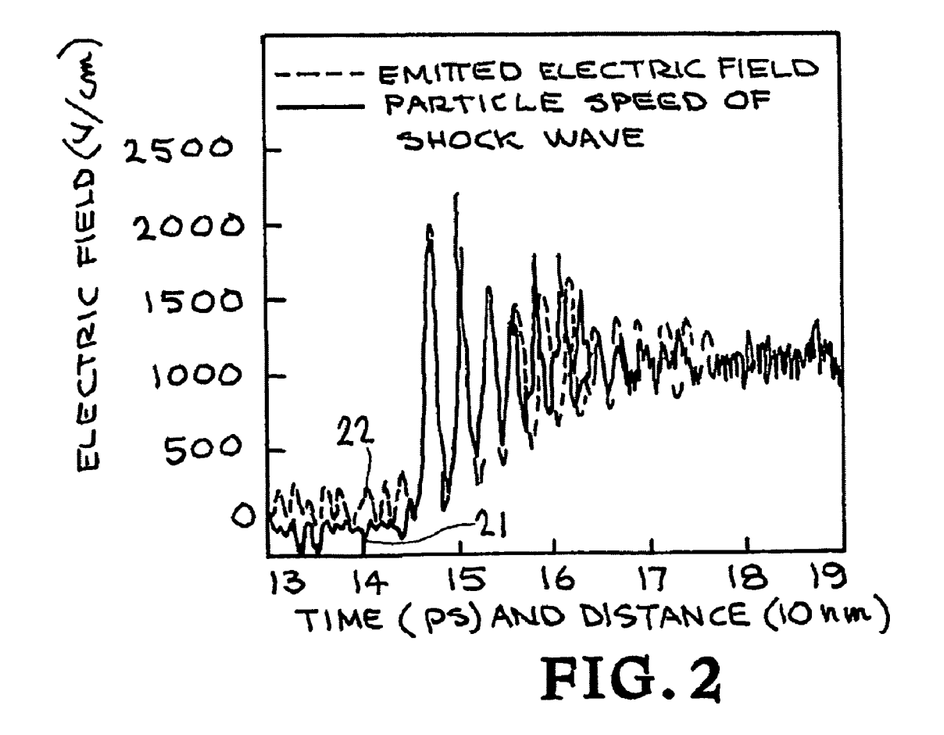
FIG. 2 is a plot showing the material velocity of the shock as a function of distance and the electric field amplitude of generated THz radiation as a function of time during a molecular dynamics computer simulation of a shock wave driven with a piston speed of 500 m/s.

FIG. 2 shows a simulation of the spatial dependence of the particle speed (closely related to the strain) for a shock wave launched into a GaN crystal. The strain profile of the shock 20 initially has no oscillatory behavior but develops oscillations after propagation through a distance of around 150 nm in this case. The number of oscillations that develop can be controlled by adjusting the temperature of the material and the propagation distance. Colder temperatures and longer propagation distances can result in more oscillations.

When the shock wave reaches an interface with another piezoelectric material, the difference in polarization currents at the interface results in a net electric polarization that can yield electromagnetic radiation. FIG. 2 shows the electric field 22 generated when the depicted shock wave propagates past a GaN/AlN interface. The time-dependence of the electric field closely resembles the spatial profile of the shock wave, i.e., more oscillations in the shock wave profile will result in more oscillations of the electric field. Larger amplitudes of the strain oscillations produce larger polarization currents and therefore larger electric field amplitudes.

Figure 3:
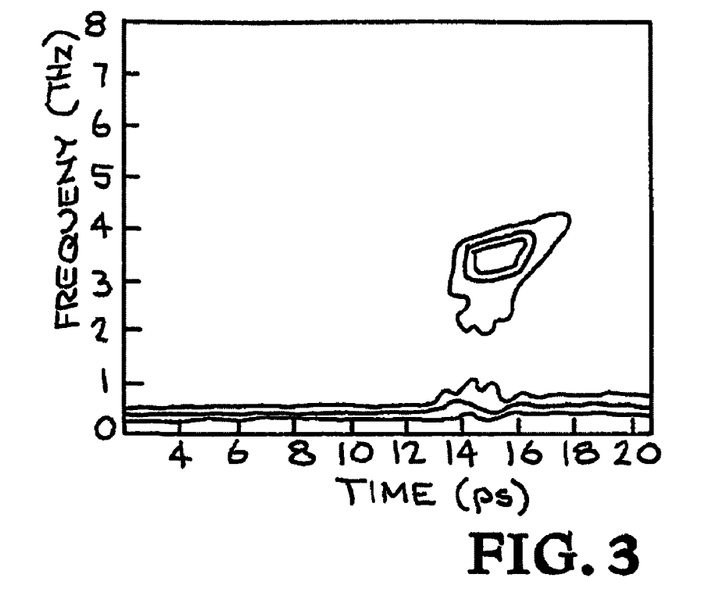
FIG. 3 shows frequency as a function of time for the electromagnetic radiation shown in FIG. 2.

FIG. 3 shows the time-dependence of the frequencies generated during the simulation of FIG. 2. The dominant frequencies are peaked around 3 THz. The frequencies produced can be varied by varying the shock pressure. Higher pressures result in higher frequency strain oscillations.

The required shock wave can be generated, e.g., using a table-top ultrafast laser with mJ or greater energy pulses [S1].

Pressures in excess of 50 GPa can be generated using such techniques. Several other techniques exist for producing THz radiation using a table-top ultrafast laser with similar energy pulses. Each has its own emission ranges and properties. These include optical rectification which generally produces broad bandwidth, short pulse radiation [S2]. Narrower bandwidth radiation has been produced from periodically poled ferroelectric crystals using rectification [S3]. Some phonon-polariton related mechanisms can also produce bursts of THz radiation that are centered around a chosen frequency [S4]. The THz electric field amplitudes of these techniques are determined by the energy density of the pump pulse which is limited by material optical damage properties.

The amplitude of the generated THz radiation is determined by the magnitude of piezoelectric properties and the amplitude of the strain waves, which is limited by plastic deformation and other mechanisms in the "hard" material. These different limiting mechanisms lead to maximum electric field amplitudes that may exceed those generated by nonlinear optical techniques for some material systems and regimes. The use of other piezoelectric materials like PZT with substantially larger piezoelectric coefficients than those of GaN and AlN yield signal amplitudes well above 10 kV/cm, generally much larger than generated through rectification. Other "hard" materials like diamond are employed to provide different THz waveforms than GaN yields.

Coherent THz frequency radiation has been predicted to be generated in a non-resonant fashion when a shock wave propagates through a crystalline material. [S5] The amplitude of the radiation generated in the present method is typically larger due to the resonant (phonon) generation mechanism. The depoling of ferroelectric materials under large amplitude shock compression has been utilized to generate strong voltage pulses above 10 kV in the RF regime peaked around a frequency on the order of 1 MHz. [S6] The method described herein utilizes spatially coherent THz frequency phonons to generate much higher frequency THz radiation.

In addition to a source of THz radiation, the invention described here also constitutes a device through which large amplitude high frequency acoustic strain waves can be converted to electromagnetic radiation and detected. This method of acoustic strain wave detection does not require the complicated and often empirical post-processing that optical reflectivity approaches require because the emission occurs only from a surface. FIG. 2 shows the direct correspondence between the emitted radiation and the strain wave in a particular case.

The generation and detection of phonons have applications including acoustical imaging of nanoscale structures in materials, phonon spectroscopy and high precision timing of acoustic and shock wave propagation through materials. Electric currents generated in piezoelectric materials have been used for decades to detect the arrival time of shock waves. However, to date, such techniques utilized electronic equipment with approximately nanosecond maximum time resolution to make measurements. The present method uses optical techniques with 100 fs or better time resolution to detect the electromagnetic radiation emitted from the currents generated in the piezoelectric material. Such high time resolution enables sensing of high frequency THz phonons.

REFERENCES

Incorporated Herein by Reference

[S1] D. S. Moore et al., App. Phys. Lett. 78, 40 (2001).
[S2] D. H. Auston et al., Phys. Rev. Lett. 53, 1555 (1984).
[S3] Y. S. Lee et al., App. Phys. Lett. 76, 2505 (2000).
[S4] R. M. Koehl et al., J. Chem. Phys. 114, 1443 (2001)
[S5] E. J. Reed et al., Phys. Rev. Lett. 96, 013904 (2006).
[S6] S. I. Shkuratov et al., Rev. Sci. Inst 75, 2766 (2004).

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Over the last decade, pioneering and innovative experiments using sub-picosecond lasers have demonstrated the generation and detection of acoustic and shock waves in materials with frequencies up to 2 THz [1-4]. In addition to groundbreaking demonstrations of acoustic solitons, these experiments lead to new techniques for probing properties of thin films and nanostructures [5-7]. Simulations of large amplitude strain and shock waves indicate that the frequencies of waves generated at shock fronts can be much higher, up to the highest acoustic phonon frequencies (around 10 THz for many materials) with spatial features as short as the atomic length scale [8-10]. However, such sharp features have never been experimentally observed, most likely due to lack of sufficient resolution in existing detection techniques. The present invention provides a method for detection of such high frequency waves for the first time. The time-dependence of the wave can be directly determined from the electromagnetic field coherently generated when it propagates past an interface between two piezoelectric materials.

It is usually assumed that electromagnetic radiation that is generated when a shock or large amplitude strain wave propagates through a material is incoherent or thermal in nature, e.g., in temperature measurements. [11] However, it has recently been predicted that temporally coherent, narrow bandwidth radiation in the THz frequency regime can emerge from a shocked crystal under some conditions [12-14] and some experimental evidence exists for other forms of electromagnetic radiation that are not incoherent. An embodiment of the present invention is a method for generating a new form of detectable coherent radiation which contains sufficient information to directly determine the time-dependence of the stress or strain in the wave.

Optical probes are commonly used to time-resolve acoustic and shock waves in materials [2, 17]. Interpretation of such experiments requires some knowledge of the high pressure dielectric properties of materials, which are generally poorly characterized or unknown at high pressures [18]. Such approaches are also limited in time resolution by a variety of mechanisms which become more prohibitive (a few ps resolution) with increasing pressure preventing observation of high frequency components above 1 THz [19]. Using molecular dynamics simulations and analytics, the present invention shows that stress waves with frequencies up to 8 THz and potentially higher can be observed when a shock wave passes a GaN/AlN heterostructure, even for high pressure shocks. Knowledge of the high pressure optical properties of the materials being probed is not required. Polarization currents generated by the high frequency strain waves at the interface can lead to emission of radiation of the strain wave frequencies.

Figure 4:
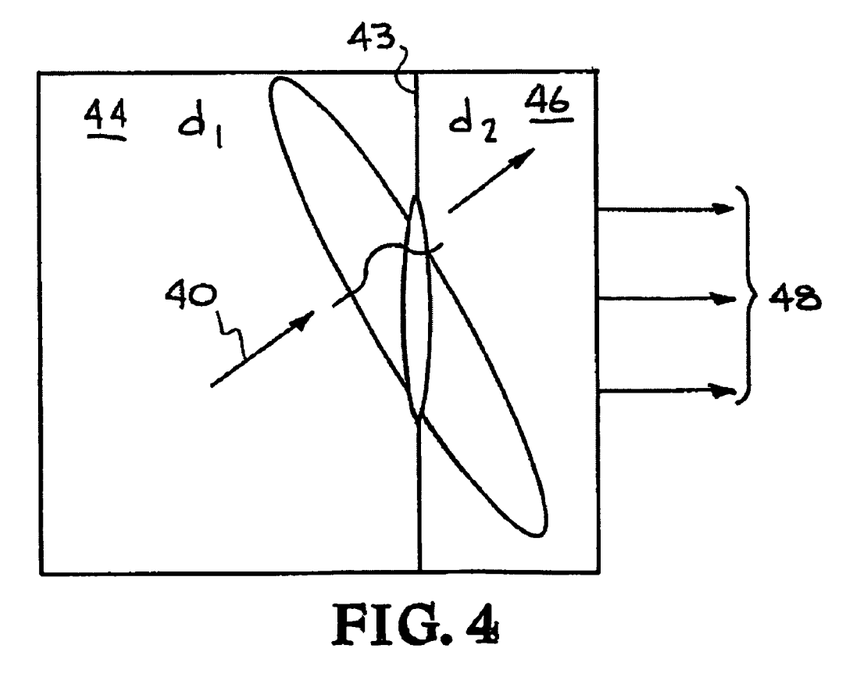
FIG. 4 is an illustration of a stress wave generating radiation as it propagates past an interface between two different piezoelectric materials with different piezo coefficients.

FIG. 4 shows schematically how a strain or shock wave 40 propagating past an interface 42 between two piezoelectric materials 44 and 46 can produce coherent radiation 48. An acoustic strain wave propagating through a uniform piezoelectric material of piezoelectric coefficient $d_1$ produces no net time-dependent electric polarization currents, i.e., $$j_{total} = \partial_t \int dz d_1 \sigma_{zz}(z - \upsilon_s t) = \text{const},$$

where $\sigma_{zz}(z-\upsilon_s t)$ is the longitudinal stress profile of the 1D wave, $\upsilon_s$ is the wave velocity, and $j_{total}$ is the polarization current per unit area. Since the electromagnetic wavelengths of interest (order of 100 μm) are much longer than the dimensions of the strain wave (order of 10 nm in the propagation direction), the strain wave does not produce non-zero frequency radiation if $j_{total}$ is constant. However, when the wave crosses an interface with another material of piezoelectric coefficient $d_2$, net polarization currents are produced of magnitude $j_{total} = \partial_t (\int_{-\infty}^{zinterface} dz d_1 \sigma_{zz}(z-\upsilon_s t) + \int_{zinterface}^{\infty} dz d_2 \sigma_{zz}(z-\upsilon_s t)) = -(d_1-d_2)\upsilon_s \sigma_{zz}(zinterface-\upsilon_s t) + \text{const}.$ [30] Since the polarization currents are directly related to the stress, radiation containing the temporal profile of the stress is coherently generated. This phenomenon bears a resemblance to so-called transition radiation that is generated when a charged particle transits an interface between two dielectric materials. For convenience, this transition radiation is referred to herein as acoustic transition radiation (ATR).

Piezoelectric materials have been employed for decades as arrival time gauges for shock wave experiments. Such techniques utilize electronics to record currents generated in the shock-compressed piezoelectric material and are limited to frequencies less than 1 GHz, precluding observation of THz signals.

The spatial distribution of radiation generated by the coherent polarization currents is determined by the spatial and spectral properties of the currents. The electric field at a point $$\vec{r}$$

generated from such polarization currents is of the form, $$\vec{E}(\vec{r}, \omega) = \int d\vec{r}' \frac{\vec{j}(\omega, \vec{r}')}{-i\omega} \left[ \frac{\left(\frac{\omega}{c}\right)^2 \hat{n} \times \hat{\varepsilon} \times \hat{n} + [3\hat{n}(\hat{n} \cdot \hat{\varepsilon}) - \hat{\varepsilon}]}{\left(\frac{1}{|\vec{r}-\vec{r}'|^2} + \frac{i\omega}{c|\vec{r}-\vec{r}'|}\right)} \right] \frac{e^{-i\frac{\omega}{c}|\vec{r}-\vec{r}'|}}{|\vec{r}-\vec{r}'|} \quad (1)$$

where $$\vec{j}(\omega, \vec{r}')$$

is the polarization current per unit area with direction $\hat{\varepsilon}$ at frequency ω at point $$\vec{r}'$$

on the interface between the two materials, i.e.

$$\vec{j}(\omega, \vec{r}') = \int dt j(t, \vec{r}') e^{-i\omega t} \text{ where } j(t, \vec{r}') = (d_1 - d_2) \upsilon_g \sigma_{zz}(t, \vec{r}').$$

When the two materials are not impedance matched, $\sigma_{zz}$ corresponds to the transmitted stress. The vector $$\hat{n} \equiv \frac{\vec{r} - \vec{r}'}{|\vec{r} - \vec{r}'|}$$

in Equation 1 (and quantities with hats) denote unit vectors. Since $$\vec{E}(\vec{r}, \omega)$$

at some point away from the shocked material can be measured in an experiment, an expression is desired for the time-dependence of the stress $\sigma_{zz}$ in terms of $$\vec{E}(\vec{r}, \omega).$$

It is assumed herein that the stress wave has the form $$\sigma_{zz}(t, \vec{r}') \equiv \sigma_{zz}(t - g(\vec{r}'))f(\vec{r}').$$

Such a form provides a description of waves including off-axis, curved, or parabolic shock fronts often generated by lasers. In this case, Equation 2 can be inverted to obtain the stress from the measured electric field, $$\sigma_{zz}(t) = \frac{1}{\upsilon_s(d_1 - d_2)} \int dt' \vec{E}(\vec{r}, t') \cdot \hat{\eta} \int d\omega i \qquad (2)$$

$$\omega e^{i\omega(t-t')} \left[ \int d\vec{r}' f(\vec{r}') e^{i\omega g(\vec{r}')} \hat{\eta} \cdot \left[ \begin{pmatrix} \left(\frac{\omega}{c}\right)^2 \hat{\eta} \times \hat{\varepsilon} \times \hat{\eta} + \\ [3\hat{\eta}(\hat{\eta} \cdot \hat{\varepsilon}) - \hat{\varepsilon}] \\ \left( \frac{1}{|\vec{r} - \vec{r}'|^2} + \\ \frac{1}{c|\vec{r} - \vec{r}'|} \right) \end{pmatrix} \frac{e^{-i\frac{\omega}{c}|\vec{r} - \vec{r}'|}}{|\vec{r} - \vec{r}'|} \right] \right]^{-1}$$

where $\hat{\eta}$ is the unit polarization of the detector at point $\vec{r}$ which is often a ZnTe or similar crystal for THz frequencies. Equation 2 provides the key result that the temporal profile of the stress of the acoustic wave $\sigma_{zz}(t)$ is unambiguously determined by the emitted electric field measured at a point in space, a function that is obtainable experimentally using existing THz technology [20].

A particularly simple case of Equation 2 arises when the size (diameter) of the shock front is much less than the wavelengths of radiation generated, i.e., $$f(\vec{r}') = A\delta(\vec{r}')$$

where A is the area of the shock front. In this case, Equation 2 becomes, $$\sigma_{zz}(t) = \frac{-|\vec{r}|c^2}{\upsilon_s A(d_1 - d_2)\hat{\eta} \times \hat{\varepsilon} \times \hat{\eta}} \int_{-\infty}^{\tau + |\vec{r}|/c} dt' \vec{E}(\vec{r}, t') \cdot \hat{\eta} \qquad (3)$$

in the radiation far-field. For larger area shock fronts, Equation 2 can be simplified considerably by employing the Fresnel approximation.

It is interesting to note that the stress can be determined by Equation 2 if the stress wave possesses a known curvature, e.g., $$g(\vec{r}') = \alpha |\vec{r}'|^2.$$

High time resolution is not destroyed by a curved shock front. The time resolution is, however, limited by the flatness of the piezoelectric interface. Nearly atomically flat interfaces can be grown for a variety of materials including GaN and AlN.

Shock waves have been shown to spontaneously generate large amplitude soliton-like oscillations in sufficiently low viscosity materials. [1, 3, 9, 10] A case is herein considered where large amplitude stress waves are generated at the front of a shock propagating down the c axis of wurzite structure GaN because it is a hard material capable of withstanding large stresses without undergoing irreversible plastic deformation of the crystal lattice. While the Hugoniot elastic limit is unknown, plastic deformation is not experimentally observed in GaN shocked along the c axis up to 13.7 GPa [21].

To study the generation of high frequency waves at shock fronts, multi-million atom molecular dynamics simulations were performed utilizing the GaN potential of Harafuji, et al. [22], which includes a Coulomb interaction [31]. Shock wave non-equilibrium molecular dynamics simulations (NEMD) were performed, which are commonly employed to study shock waves in a variety of materials [23]. Planar shock waves are generated within 3D computational cells of crystalline atoms with cross section 11×12 nm and length in the shock propagation direction about 300 nm by constraining atoms at one edge of the long dimension of the computational cell to move into the cell like a planar piston (representing the mechanical driving force or object that generates the shock) [32].

Figure 5:
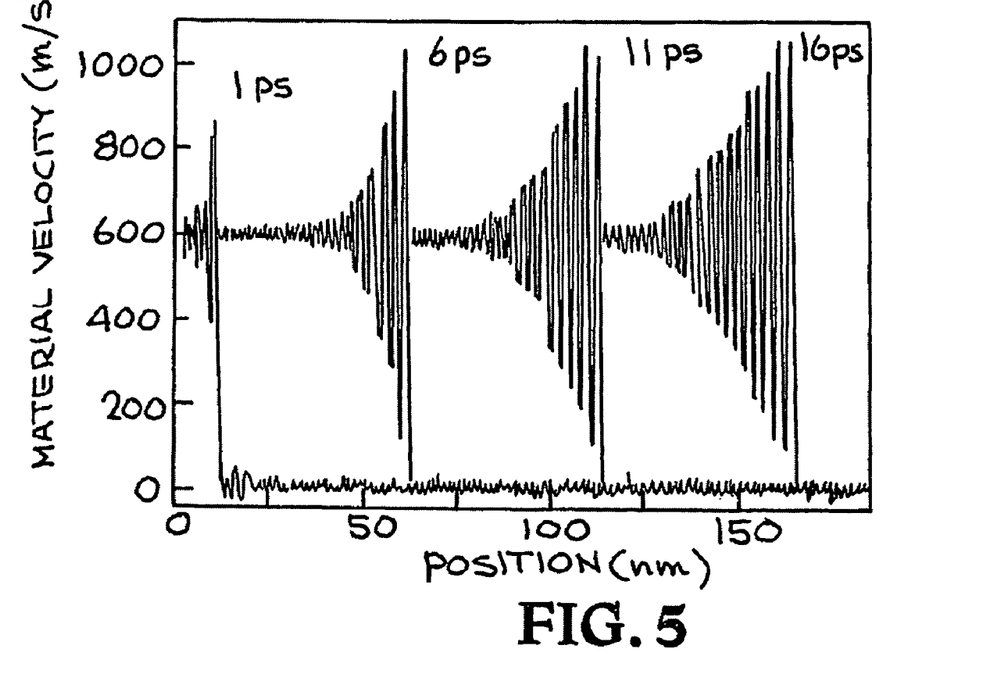
FIG. 5 shows the spontaneous formation of large amplitude, THz frequency oscillations in material speed (related to strain) during a molecular dynamics simulation of a shock wave propagating through GaN.

FIG. 5 shows the material speed in a molecular dynamics simulation of a wave driven down the c axis of wurzite GaN. The wave is steepening and developing high frequency oscillations as it propagates. The average strain in this shock is about −0.06 corresponding to an average stress in the shock direction of around 24 GPa. The wave is generated with a monotonic rise in piston speed to 600 m/s but large amplitude oscillations form spontaneously and increase in number as the wave propagates. The amplitude of the oscillations is extremely large, nearly 0.12 in strain. Such oscillations also occur at smaller piston speeds and when the piston is ramped up to its final speed more slowly, over several picoseconds. Spontaneous oscillation formation at a shock front can occur when the shock deposits most of its energy into specific acoustic phonon modes and the subsequent coupling of this energy to other phonon modes (dephasing) is much slower than the timescale of the acoustic phonon period. Such effects are most pronounced at lower temperatures under high symmetry conditions in crystals where coupling is reduced by symmetry. Quasi-soliton effects at shock fronts can be also understood within the context of the inverse scattering formalism summarized in Ref. [1]. Such shock waves can be generated experimentally using a table-top ultrafast laser with mJ or greater energy pulses [24].

To study ATR when the wave in FIG. 5 reaches a GaN/AlN interface, the interatomic potential of Harafuji, et al. [22] is utilized for both the GaN and AlN because wurzite AlN has lattice and elastic properties within a few percent of those of GaN (see e.g., Ref. [25] for a comparison.) Polarization currents at the frequencies of interest were calculated directly from the molecular dynamics simulations, $$j(t) = \frac{1}{A} \sum_i \upsilon_{z,i}(t) q_i$$

where $q_i$ is an atomic charge, $\upsilon_{z,i}$ is the shock direction (z) component of the velocity of atom i, and A is the cross sectional area of the computational cell [33].

Figure 6A:
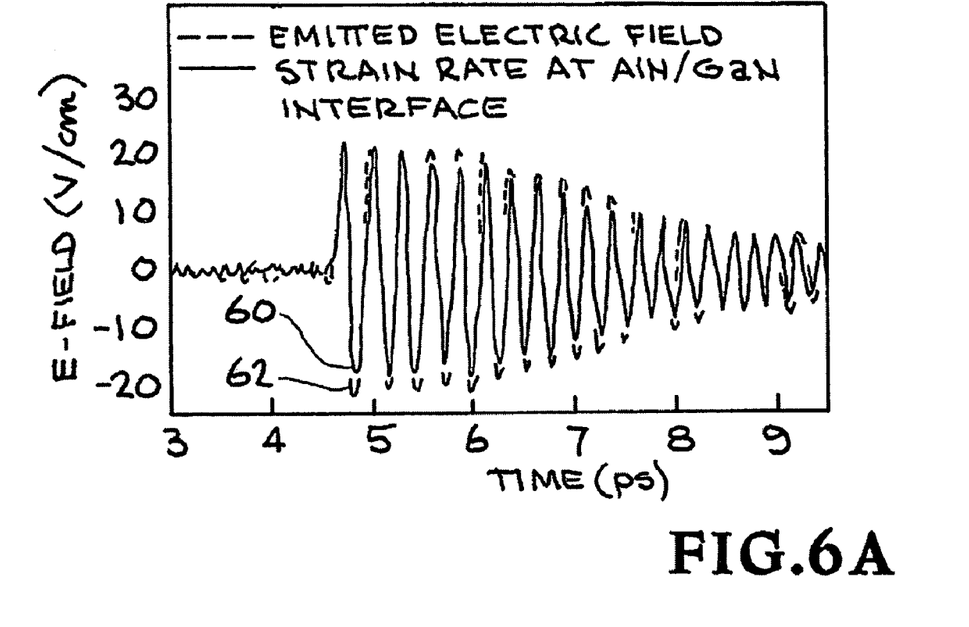
FIG. 6A shows the strain rate in a molecular dynamics simulation at an AlN/GaN interface compared to the calculated electric field measured 1 mm from the interface for a shock wave.

FIG. 6A shows close agreement between the AlN strain rate 60 adjacent to the AlN/GaN interface and the emitted electric field amplitude 62 1 mm from the shock wave of FIG. 5. The strain rate (time-derivative of strain) is nearly proportional to $\dot\sigma_{zz}(t)$. The diameter of the planar shock front is 50 μm and the electric field is measured in the shock plane, computed using Equation 1 in the limit of a point dipole shock. It is assumed that the GaN/AlN heterostructure is sufficiently thin to not affect radiation propagation at these frequencies.

Figure 6B:
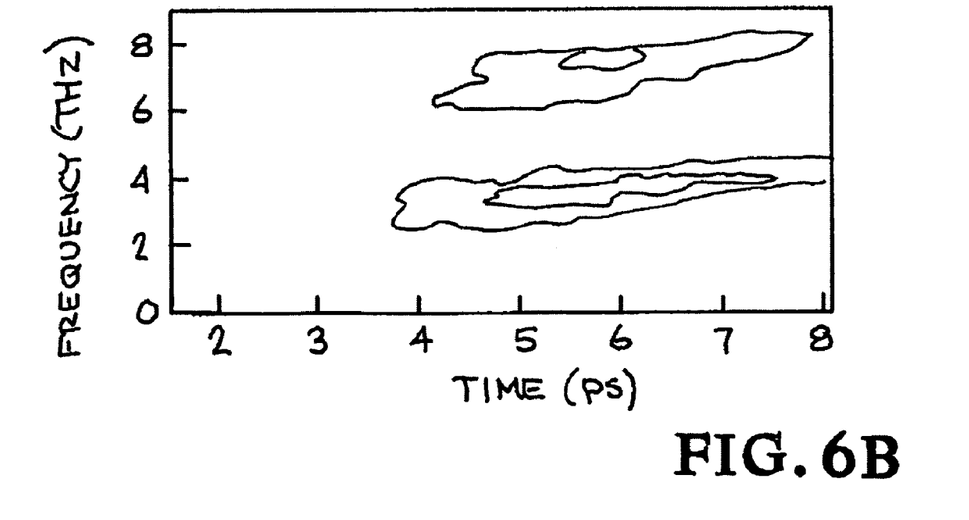
FIG. 6B shows frequency as a function of time for the electromagnetic radiation of the simulation parameters used in FIG. 6A.

FIG. 6B shows the time-dependence of the frequencies present in the electric field generated in FIG. 6A. The frequencies are slightly chirped with a fundamental around 4 THz and a harmonic around 8 THz. The 8 THz spectral components correspond to half cycle spatial features of around 5 Å which is close to the interatomic spacing. Therefore the emitted THz contains sufficient spectral information to provide atomic scale resolution of the wave. It has been observed that lower shock pressures yield lower frequencies.

Figure 7A:
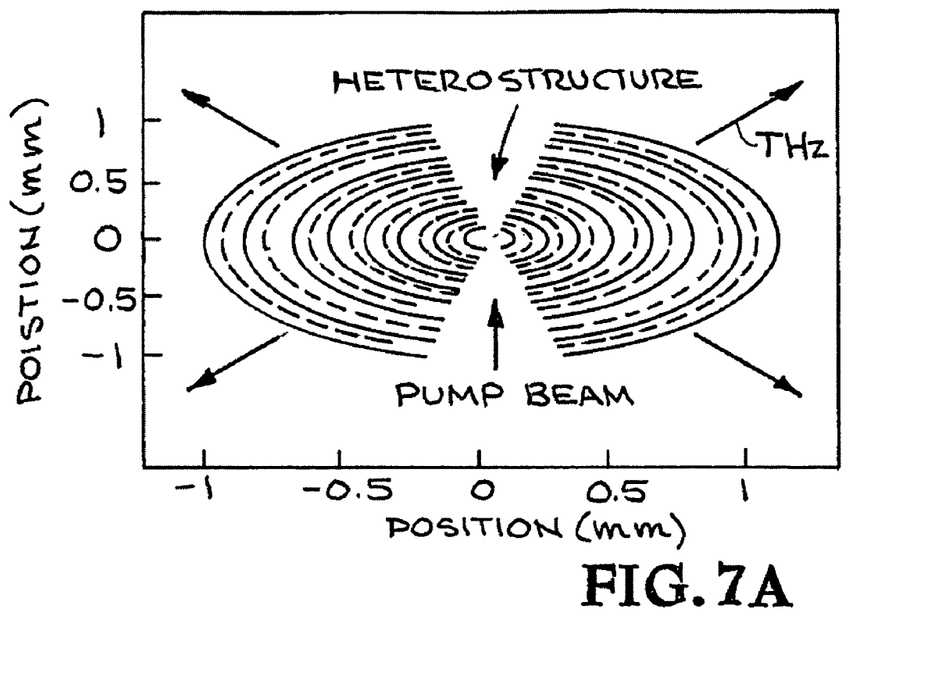
FIG. 7A shows calculated radiation generated from the stress wave having a shock front diameter of 50 μm.
Figure 7B:
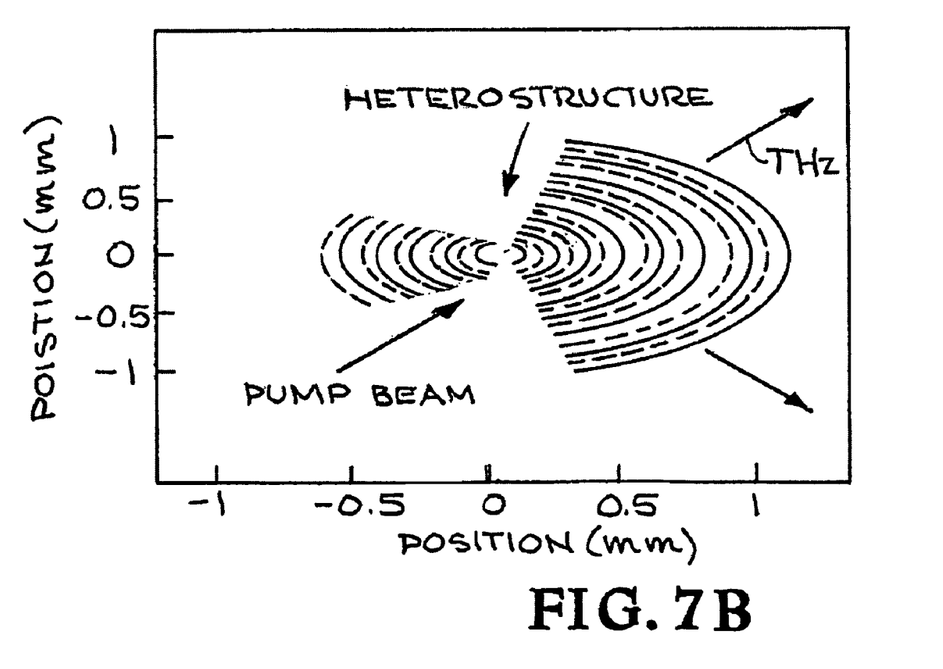
FIG. 7B shows calculated radiation generated from the stress wave having a shock front diameter of 300 μm and a non-normal incidence.

FIG. 7A shows the far field spatial distribution of the electric field generated for the case of a 50 μm diameter shock $$f(\vec{r}') = e^{-|\vec{r}'|^2/\beta^2}$$

with β=25 μm in Eq. 1). The radiation exhibits a dipole pattern with the shock at the center. FIG. 7B shows the electric field for the case of a shock front diameter of 300 μm (β=150 μm) and a slightly off-axis propagation of the shock. A tilt can be induced in the shock front by angling the pump beam as shown in the case of a laser-driven shock wave. The radiation is directed for this larger diameter shock resulting in higher field amplitudes than the case in FIG. 7A, on the order of hundreds of V/cm.

ATR can be observed in other types of materials including non-piezoelectrics, although likely to be of lower amplitude. In general, the gradient in stress at a shock front can break inversion symmetry establishing a static polarization at the front of a shock in any material. Such effects are well known and have been observed in experiments at lower frequencies (see e.g., Ref. [26-28]). Finally, this effect provides a useful source of THz radiation for some applications since it is directable, frequency tunable by varying the shock pressure, and the number of cycles can be tuned by varying the propagation distance.

Methods for detecting THz radiation are known in the art. For example, to detect THz radiation via electro-optic sampling using an 800 nm wavelength, 100 fs duration, linearly polarized probe, the probe is copropagated with the THz emission through a ZnTe nonlinear crystal. ZnTe is normally optically isotropic, but an applied electric field induces birefringence in the crystal. This optical birefringence makes the linearly polarized probe light slightly elliptical, in proportion to the strength of the copropagating THz electric field. Ultimately, the ellipticity of the probe is detected, and the THz electric field is inferred from the THz radiation induced probe ellipticity.

To reduce laser noise in the measurement of the probe ellipticity, a method called differential detection is used (cf. G. Zhao et al., Review of Scientific Instruments, 73 (2002) 1715), where the elliptically polarized probe passes through a quarter wave plate, which brings the polarization to near circular, and then passes through a polarizing beam splitter, which splits the probe beam into its two component polarizations. The power in these two beams are then detected and electronically subtracted to give the signal. For a given sign of the probe ellipticity before passing through the quarter wave plate, the power of the S-polarized beam (after the quarter wave plate) will be the sum of a large background signal and a small signal with the same sign as the original probe ellipticity. In contrast, the power of the P-polarized beam will be the sum of the same large background and a small signal with the opposite sign as the original probe ellipticity. Taking the difference between these two signals results in the cancellation of the large background (and noise associated with this background) resulting in a substantial increase in detection sensitivity.

REFERENCES

Incorporated Herein by Reference

[1] H. Y. Hao and H. J. Maris, Phys. Rev. B 64, 064302 (2001).
[2] K. T. Gahagan, D. S. Moore, D. J. Funk, R. L. Rabie, and S. J. Buelow, Phys. Rev. Lett. 85, 3205 (2000).
[3] O. L. Muskens and J. I. Dijkhuis, Phys. Rev. Lett. 89, 285504 (2002).
[4] O. L. Muskens, A. V. Akimov, and J. I. Dijkhuis, Phys. Rev. Lett. 92, 035503 (2004).
[5] C. Thomsen, H. T. Grahn, H. J. Maris, and J. Tauc, Phys. Rev. B 34, 4129 (1986).
[6] H. J. Maris, Sci. Am. 278, 86 (1998).
[7] T. Saito, O. Matsuda, and O. B. Wright, Phys. Rev. B 67, 205421 (2003).
[8] D. H. Robertson, D. W. Brenner, and C. T. White, Phys. Rev. Lett. 67, 3132 (1991).
[9] V. V. Zhakhovskii, S. V. Zybin, K. Nishihara, and S. I. Anisimov, Phys. Rev. Lett. 83, 1175 (1999).
[10] S. V. Zybin, M. L. Elert, and C. T. White, Phys. Rev. B 66, 220102(R) (2002).
[11] G. W. Collins, P. M. Celliers, L. B. D. Silva, R. Cauble, D. M. Gold, M. E. Foord, N. C. Holmes, B. A. Hammel, R. J. Wallace, and A. Ng, Phys. Rev. Lett. 87, 165504 (2001).
[12] E. J. Reed, M. Soljačić, R. Gee, and J. D. Joannopoulos, Phys. Rev. Lett. 96, 013904 (2006).
[13] E. J. Reed, M. Soljacic, and J. D. Joannopoulos, Phys. Rev. E 75, 056611 (2007).
[14] E. J. Reed, M. Soljacic, R. Gee, and J. D. Joannopoulos, Phys. Rev. B 75, 174302 (2007).
[15] B. Hayes, J. Appl. Phys. 38, 507 (1967).
[16] C. J. Stanton, G. D. Sanders, R. Liu, G. W. Chern, C. K. Sun, J. S. Yahng, Y. D. Jho, J. Y. Sohn, E. Oh, and D. S. Kim, Superlattices and Microstructures 34, 525 (2003).
[17] J. E. Patterson, A. Lagutchev, W. Huang, and D. D. Dlott, Phys. Rev. Lett. 94, 015501 (2005).
[18] R. E. Setchell, J. Appl. Phys. 91, 2833 (2002).
[19] P. J. S. van Capel and J. I. Dijkhuis, Appl. Phys. Lett. 88, 151910 (2005).
[20] B. Ferguson and X. C. Zhang, Nature Mat. 1, 26 (2002).
[21] H. Y. Peng, M. D. McCluskey, Y. M. Gupta, M. Kneissl, and N. M. Johnson, Appl. Phys. Lett. 82, 2085 (2003).
[22] K. Harafuji, T. Tsuchiya, and K. Kawamura, J. Appl. Phys. 96, 2513 (2004).
[23] A. Strachan, A. C. T. van Duin, D. Chakraborty, S. Dasgupta, and W. A. Goddard, Phys. Rev. Lett. 91, 098301 (2003).
[24] D. S. Moore, K. T. Gahagan, J. H. Reho, D. J. Funk, S. J. Buelow, and R. L. Rabie, App. Phys. Lett. 78, 40 (2001).
[25] O. Ambacher, J. Majewski, C. Miskys, A. Link, M. Hermann, M. Eickhoff, M. Stutzmann, F. Bernardini, V. Fiorentini, V. Tilak, B. Schaff, and L. F. Eastman, J. Phys.: Cond. Mat. 14, 3399 (2002).
[26] G. E. Hauver, J. Appl. Phys. 36, 2113 (1965).
[27] R. K. Linde, W. J. Muri, and D. G. Doran, J. Appl. Phys. 37, 2527 (1966).
[28] P. Harris and H. Presles, J. Chem. Phys. 77, 5157 (1982).
[29] S. J. Plimpton, J. Comp. Phys. 117, 1 (1995).
[30] Here we consider the two materials to be acoustically impedance matched for simplicity.

[31] A particle-particle particle-mesh approach is utilized with the LAMMPS molecular dynamics code. [29]

[32] The compressive shock changes the total static polarization of the crystal in the c axis direction to the piezoelectric effect. To prevent artificial compensating electric fields from being applied by the periodic boundary conditions in this direction, a computational cell which contains a mirror image of the shocked GaN crystal is utilized so that the total polarization of the computational cell remains constant, discussed in Ref. [12]

[33] Effective charge magnitudes of 0.676 for the GaN material and 1.612 for the AlN material were utilized in this sum to reproduce experimental piezeoelectric coefficients. While thermal noise is not significant under experimental conditions, observation of the coherent signal above thermal noise requires computational cell cross section dimensions on the 10 nm scale or greater.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:
providing a first piezoelectric material in contact with a second piezoelectric material to form an interface, wherein said first piezoelectric material comprises a first piezoelectric coefficient and wherein said second piezoelectric material comprises a second piezoelectric coefficient, wherein said first piezoelectric coefficient is different from said second piezoelectric coefficient; and
generating a shock wave in said first piezoelectric material, wherein said shock wave comprises THz frequency oscillations, wherein said THz frequency oscillations are converted to electric polarization currents at said interface, wherein THz electromagnetic radiation is generated with temporal behavior matching that of said shock wave.

2. The method of claim 1, wherein the step of producing strain oscillations includes directing a laser beam onto said first material.

3. The method of claim 1, wherein said first material is selected from a group consisting of GaN, AlN and diamond.

4. The method of claim 1, wherein said first material comprises GaN and said second material comprises AlN.

5. The method of claim 1, wherein said first material comprises AlN and said second material comprises GaN.

6. The method of claim 1, further comprising detecting said electromagnetic radiation.

7. The method of claim 1, further comprising determining the temporal behavior of said strain oscillations from said temporal behavior of said electromagnetic radiation.

8. The method of claim 1, wherein said electromagnetic radiation comprises a wavelength within a range from about 100 μM to about 1 mm.

9. The method of claim 1, further comprising an ablation layer attached to said first material, wherein the step of producing strain oscillations in a first material includes ablating at least a portion of said ablation layer.

* * * * *